(12) United States Patent
Ning

(10) Patent No.: US 8,547,423 B2
(45) Date of Patent: Oct. 1, 2013

(54) IMAGING SYSTEM AND DEVICE

(76) Inventor: Alex Ning, Carlsbad, CA (US)

( * ) Notice: Subject to any disclaimer, the term of this patent is extended or adjusted under 35 U.S.C. 154(b) by 522 days.

(21) Appl. No.: 12/888,325

(22) Filed: Sep. 22, 2010

(65) Prior Publication Data

US 2011/0069160 A1    Mar. 24, 2011

Related U.S. Application Data

(60) Provisional application No. 61/245,565, filed on Sep. 24, 2009.

(51) Int. Cl.
  *A62B 1/04*    (2006.01)
(52) U.S. Cl.
  USPC ............................................................ 348/65
(58) Field of Classification Search
  USPC .................... 348/65, 36, 21.6, 335; 345/32
  IPC ...................................................... A62B 1/04
  See application file for complete search history.

(56) References Cited

U.S. PATENT DOCUMENTS

| | | | |
|---|---|---|---|
| 5,313,306 A | | 5/1994 | Kuban et al. |
| RE36,207 E | | 5/1999 | Zimmermann et al. |
| 6,005,611 A | * | 12/1999 | Gullichsen et al. ........ 348/211.6 |
| 6,795,113 B1 | | 9/2004 | Jackson et al. |
| 7,042,497 B2 | | 5/2006 | Gullichsen et al. |
| 7,042,508 B2 | * | 5/2006 | Jan et al. ........................ 348/335 |
| 7,274,381 B2 | | 9/2007 | Mojaver et al. |
| 7,427,263 B2 | | 9/2008 | Hoeg et al. |
| 2004/0012544 A1 | * | 1/2004 | Swaminathan et al. ........ 345/32 |
| 2006/0285002 A1 | | 12/2006 | Robinson et al. |
| 2007/0126892 A1 | | 6/2007 | Guan |
| 2009/0059041 A1 | | 3/2009 | Kwon |
| 2010/0033551 A1 | * | 2/2010 | Agarwala et al. ............... 348/36 |

OTHER PUBLICATIONS

Hynek Bakstein, Tomas Pajdla, Panoramic mosaicing with a 180 field of view lens, center for machine perception, czech technical university, Prague, czech republic, Jun. 2002.

Jie Jiang, et al, Distortion Correction for a wide-angle lens based on real-time digital image processing, Optical Engineering, vol. 42 No. 7, Jul. 2003 p. 2029-2039, Society for photo optical engineers (Jul. 2003) SPIE Digital Library.

* cited by examiner

*Primary Examiner* — Gims Philippe
(74) *Attorney, Agent, or Firm* — Mark Wisnosky

(57) ABSTRACT

An imaging system and method of application, including lens designs tailored to be used with particular transformation algorithms, electronic hardware and algorithms for image transformations is described. Exemplary application of the system including automotive, photographic and medical endoscopic are also described. The system enables improved image view and allows customization of views by the end user even after installation of the image system hardware.

25 Claims, 13 Drawing Sheets

$\beta_2 = 0.95$ $\beta_2 = -0.95$ $\beta_2 = 0.83$ $\beta_2 = -0.50$ $\beta_2 = 0.77$ $\beta_2 = 0.20$ $\beta_1 = 0.67$

IMAGING SYSTEM AND DEVICE

CROSS-REFERENCE TO RELATED APPLICATIONS

This application claims the benefit of U.S. Provisional Patent Application 61/245,565, filed Sep. 21, 2009, entitled "Wide-Angle Imaging System and Device", currently pending, by the same inventor, and incorporated by reference.

BACKGROUND OF THE INVENTION

1. Technical Field

The present invention relates to an imaging system and devices for medical, automotive, photographic and other applications.

2. Related Background Art

Wide-angle lenses are useful for a variety of applications including medical application such as endoscopes, security cameras, automotive cameras and imaging systems for photography. As the field of view increases, geometric lens distortion becomes un-avoidable. The straight lines at the off-axis field points become curved. Distortion can be minimized with appropriate lens design. Lenses are also designed with particular geometric distortion properties to match the application. Lenses may be designed to provide the best overall visual appearance and the ability to detect details in particular regions of the image. Such lenses, termed here as, Tailored Distortion Lenses, reduce distortion optically by using a combination of spheric and aspheric elements. However, sometimes significant amount of distortion can still be easily seen even in a tailored distortion lens. To further reduce the distortion of a tailored distortion lens through the design of the optics is very difficult and may require undesirable compromises of other lens parameters. However the remaining distortion can be further reduced or optimized for particular applications or particular situations in an application by processing the image data. The processed image is then displayed to the user or saved to a memory for further processing. The resulting image will have less distortion than what can be accomplished optically alone. For certain applications, the resulting images provide better views of important features, are most pleasing to view and appear more natural to the users.

Zooming is a common feature in many imaging systems. There are two ways to accomplish zooming: optical or digital. In an optical zoom, the components (lens elements, spacers, etc) are moved physically to cause a change in the overall focal length of the system. For example, a typical consumer camera employs an optical zoom lens having moving lens groups. For a given image size (film or the imaging sensor), this means that the overall field of view of the system is also changing during zooming. The field of view is reduced for increased focal length and vice versa. Digital zooming is a process in which a smaller section of an image is enlarged to fill the entire available area of the display. When a smaller section is enlarged, one loses field of view because image areas outside the zoomed area can no longer be displayed. There is a need to zoom in on an area of interest, yet simultaneously be able to see the full field of view.

Corrections of the geometric distortion heretofore required algorithms specific to each lens design. There is a need for an algorithm that accurately and generally describes lens behavior. With such a function there would be a reduced need to design a custom lens for each application. Similarly, heretofore color and geometric corrections have been accomplished in software through empirical measurements and numeric approximation of the lens mapping. Often the lens mapping function is described as a polynomial expansion containing multiple empirically determined terms specific to the particular lens. Measurements for calculating the particular algorithms require use of data from broad areas of the lens. In other cases a linear approximation for lens behavior is used that is good for only a narrow section of the image. There is a need for a descriptive function of lens behavior that applies to multiple lens designs, is applicable to the entire viewing region of the lens and can be calculated using data from a narrow region of the lens. This makes the embedding of processing algorithms easier for certain types of electronic imagers.

The image from a single lens can be modified to simulate the behavior of a different lens. Applications such as endoscopy require particular lens designs for particular procedures or even for portions of procedures. In some cases there is a need to retract a probe and change the lens or exchange the probe for another with a different lens for a different stage of the procedure. This adds to the complexity of procedures and increases the chance for contamination and infection. Complex mechanical lens elements have been used to enable a modification of the field or direction of view to help enable a single probe to be used throughout a procedure or for multiple procedures. The tradeoff is most often a smaller field of view for the ability to image a limited area. These more complex probes can often lead to a surgeon missing particular features as the field of view is narrowed or the field of view is limited to a particular direction. There is a need for endoscopic probes that can smoothly change the field of view or can smoothly change the image from one lens design to another without the need to physically change the probe.

Wide-angle lenses are also finding increasing use in automotive applications. Imaging systems incorporating wide-angle lenses are used for viewing the region behind a vehicle to eliminate blind spots unavoidable with mirrors or simply the view out the rear window. Geometric distortions in such images may result in effectively blind spots similar to those that the systems are intended to eliminate. The most effective image for driver viewing also varies by the driving situation, the particular drivers, and even driver preferences. There is a need to be able to transform the image of an automotive camera after the camera has been installed in the vehicle. There is additionally a need to be able for the driver to easily transform the image to match a changing driving situation.

There is a need for the ability to process the images captured by an electronic imager to provide modifications of the geometric distortions to the viewed image. There is a need for an image processing method, which accurately describes lens behavior and uses only a minimum number of parameters to characterize the lens mapping function. There is a need for an imaging system that uses lens designs that are tailored to the processing algorithms used to subsequently manipulate the image.

Attempts to provide algorithms have been reported in, for example, U.S. Pat. Re. 36,207, U.S. Pat. No. 7,427,263, U.S. Pat. No. 7,042,508 and U.S. Pat. No. 7,042,497. None of these attempts address the needs discussed above.

DISCLOSURE OF THE INVENTION

In one embodiment a new "zooming" method is disclosed. This new zooming method allows one to enlarge or shrink the central section of the image while still preserving the overall field of view. Applications of this invention are in imaging systems such as endoscopes, automotive applications and security cameras. Zooming while maintaining the field of view is accomplished with digital processing hardware and software. An image (video frame) is captured by a lens having known optical properties. This image is processed digitally to enlarge or shrink the central portion of the image producing a transformed image. In one embodiment the calculation is constrained such that the transformed image will have the same overall field of view as the originally acquired image. This means that the off-axis image is squeezed or stretched to accommodate the zooming of the central portion of the image. The transition between center and periphery is smooth and continuous. While the central portion is "zoomed in", the periphery is "zoomed out" and vice versa. The image is captured by an electronic imager (for example, a CCD or CMOS imager) located at the focal plane of the lens. The electronic image is then manipulated using processing algorithms programmed into the same processor that acquires the images or optionally a second processor. The second processor may be remotely located from the processor that acquires the images initially.

The invention is applicable and claimed for a range of lens systems. Preferred embodiments include a wide-angle lens system. As used herein a "wide-angle" lens system refers to a lens with a filed of view equal to or greater than approximately 100 degrees.

Yet another embodiment of the invention allows for simulation of the image that would be obtained by a target lens system having a particular set of design parameters using actual image data from a different lens having different design parameters from the target lens system and calculating the simulated or transformed image data by applying a transformation to the actual image data. The simulation is effected by applying an image processing algorithm herein termed a distortion transformation, to map the image obtained using the actual lens system onto a simulated image from the target lens design.

Another embodiment of the invention uses lens that follow a new parametric equation for the lens mapping function. The constraint of following this lens mapping function in conjunction with the design parameters of the physical size of the lens, number of lens elements and the desired field of view will provide a solution for the lens design. A lens made to these design parameters is then used in an imaging system comprising additionally a sensor and a processor to acquire an image and means to provide user inputs. The processor is further programmed to accomplish coordinate transformations upon the acquired image based upon user inputs. The transformations allow improved analysis of the images through a reduction or increase in the apparent distortions and ability to zoom the image, while maintaining all available data. In another embodiment the processing of the image is done remotely from the location of acquiring the image. In another embodiment separate processors are used to acquire the image and to manipulate the image based on user inputs.

Another embodiment of the invention is a system for accomplishing image coordinate transformation to map the pixels of an imager device attached to a lens system to an arbitrary display format for viewing. Such transformations allow for the correction of distortions introduced by the lens system in conventional display formats and for the projection of images onto custom display formats as used, for example, in simulators and games.

Another embodiment of the present invention is an imaging system comprising a lens system, an image sensor, hardware and software for an image acquisition and processing system that accomplishes image storage and the zooming and coordinate transformation techniques described above, and a display.

Another embodiment of the invention introduces lenses that are specifically designed to follow a novel lens mapping function. The constraint of the lens mapping function and design parameters such as the dimensions of the lens, the number of lens elements and the target field of view, define a recipe for a lens that is particularly suitable for acquiring images that are to be further manipulated through described coordinate transformations.

Another embodiment of the invention uses lens that follow a new parametric equation for the lens mapping function. The constraint of following this lens mapping function in conjunction with the design parameters of the physical size of the lens, number of lens elements and the desired field of view will provide a solution for the lens design. A lens made to these design parameters is then used in an imaging system comprising additionally a sensor and a processor to acquire an image and means to provide user inputs. The processor is further programmed to accomplish coordinate transformations upon the acquired image based upon user inputs. The transformations allow improved analysis of the images through a reduction or increase in the apparent distortions and ability to zoom the image, while maintaining all available data.

MODES FOR CARRYING OUT THE INVENTION

The term "lens element" means a single transparent mass of refractive material having two opposing refracting surfaces. An aspheric element is a lens element having at least one refracting surface that is neither spherical nor flat. The term "lens component" is defined as (a) a single lens element spaced so far from any adjacent lens element that the spacing cannot be ignored in computing the optical properties of the lens assembly, or (b) two or more lens elements that have their adjacent lens surfaces either in full overall contact or overall so close together that the spacing between adjacent lens surfaces can be ignored in computing the overall lens assembly performance. Lens elements and lens components are identified numerically increasing from object to image.

Figure 1:
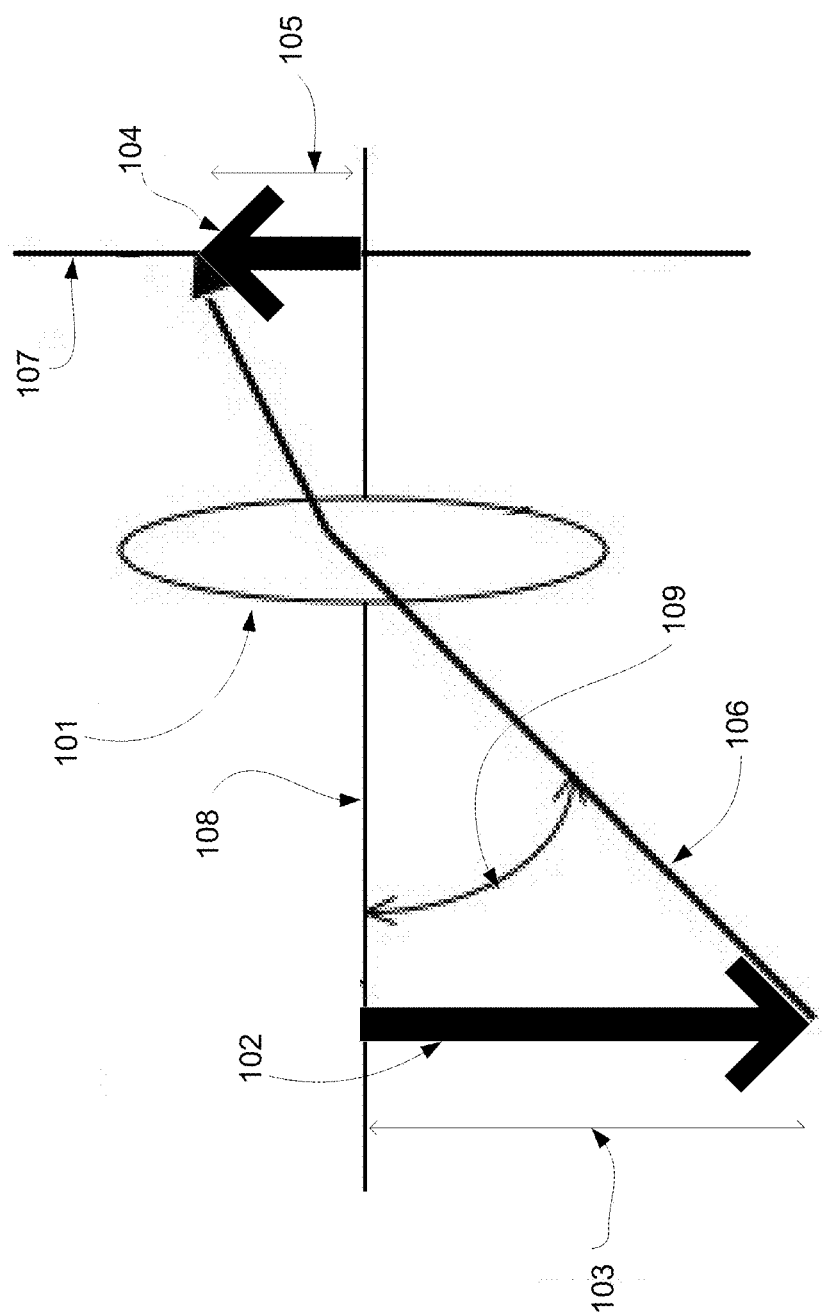
FIG. 1 shows a rudimentary lens and imaging system.

FIG. 1 shows the functionality of a lens. An object 102 is imaged by a lens system 101 having an optical axis 108. The lens system 101 may consist of a single lens element or multiple lens elements. A single element is shown only for purposes of illustration in FIG. 1 and it is to be understood the lens system 101 may in fact consist of multiple lens elements. An off-axis ray 106 from the object at a height 103 from the optical axis hits the lens entrance pupil center at field angle θ 109 (angle between the optic axis and chief ray). This ray is then refracted towards the focal plane 107 where an electronic imager is located (not shown). The lens system produces an image 104 of the object at the focal plane. Non-limiting examples of electronic imagers or sensors include complimentary metal oxide semiconductor (CMOS) imagers and charge coupled device (CCD) imagers. The off-axis ray 106 is focuses on the image plane at a height or distance 105 from the optical axis. The ray height h 105 is defined as the distance between the chief ray intercept with the focal plane, and the optic axis 108. Only a single ray is shown but it should be understood that the image 104 is composed of multiple rays from the object each imaged at the focal plane at a distance from the optical axis, said distance determined by the characteristics of the lens. The mathematical relationship between the image height h and the field angle θ for each of these rays is known as the lens mapping function. The combination of a lens or system of lenses, an image sensor typically located at the focal plane of the lens, and electronics to capture images and processor for transforming images is an imaging system or imager. This lens mapping function defines the image height "h" as a function of θ where h(θ) is the image height shown in FIG. 1 as the distance from the top of the image 105 to the optical axis 108. The top of the image 105 is located by the off-axis chief ray 106 that enters center of the pupil at the optical axis 108 with the field angle θ expressed in radians. The parameter "f" is the paraxial effective focal length of the—objective lens, and it is measured on the optical axis 108 with an infinitesimally small bundle of rays.

For standard lenses with negligible distortion, the lens mapping function is as follows:

$$h(\theta)=f*\tan(\theta) \tag{1}$$

where f is the effective focal length of the lens. Lenses that follow this mapping function are known as "rectilinear" lenses. Wide-angle and fisheye lenses do not follow this equation well. A commonly used mapping function for fisheye lenses is:

$$h(\theta)=f*\theta \tag{2}$$

Lenses that follow Eq (2) are known as "f-θ" or "equidistant" lenses. This equation is generally used in commercial software for de-warping images taken by fisheye lenses. The recently invented Tailored Distortion lenses by the same inventor do not follow this equation well. Most wide angle lenses do not follow this equation closely. But it is used as an approximation to the lens mapping function over a narrow field of view. A general approach is to use a high-order polynomial as follows to characterize the lens mapping function.

$$h(\theta)=a1*\theta+a2*\theta^2+a3*\theta^3+a4*\theta^4+\ldots \tag{3}$$

where θ is given in radians. The coefficients a1, a2, a3 ... are empirically determined from the lens design by fitting a polynomial to the actual curve of h vs. θ of the lens. Though Eq (3) is a very general technique for characterizing any lenses, it requires typically more than 4 coefficients to achieve a reasonable fit. Fitting more than 4 parameters requires use of test patterns that use a significant portion of the field of view of the lens.

In the present invention, we introduce a new mapping function for characterizing lenses:

$$h(\theta)=(f/\beta)*\tan(\beta*\theta) \text{ for } \beta>0 \tag{4a}$$

$$h(\theta)=(f/\beta)*\sin(\beta*\theta) \text{ for } \beta<0 \tag{4b}$$

where f is the effective focal length of the lens, and β is termed as "rectilinearity". The rectilinearity β can be determined from any lens design program such as Zemax®, Zemax is a registered trademark of Zemax Development Corporation. In practice, β is the best-fit value that approximates the actual h(θ) vs. θ curve of the lens. Rectilinearity represents the degree of distortion in lenses. If β=1, Eq (4a) becomes Eq (1), the mapping function of distortion-free lens. When β approaches 0, either Eq (4a) or (4b) becomes Eq (2), the mapping function of a perfect "f-θ" lens. It must be noted that the image formed by a perfect f-θ lens will still look distorted, i.e. the off-axis objects are "squeezed" relative to the on-axis objects. Using the f-θ lens as a baseline reference, most commercially available wide-angle lenses "squeeze" the off-axis objects even more. Their β values are negative. The tailored distortion lenses "squeeze" off-axis objects less and have positive β values. The advantage of Eq (4a) and Eq (4b) over Eq. (3) is that it allows one to model the behavior of a lens using only two parameters. It is easier and more efficient to implement in software (either stand alone or embedded in hardware processors). In subsequent discussions reference to the lens mapping function will equivalently refer to equations 4a and 4b or simply equation 4.

Figure 2:
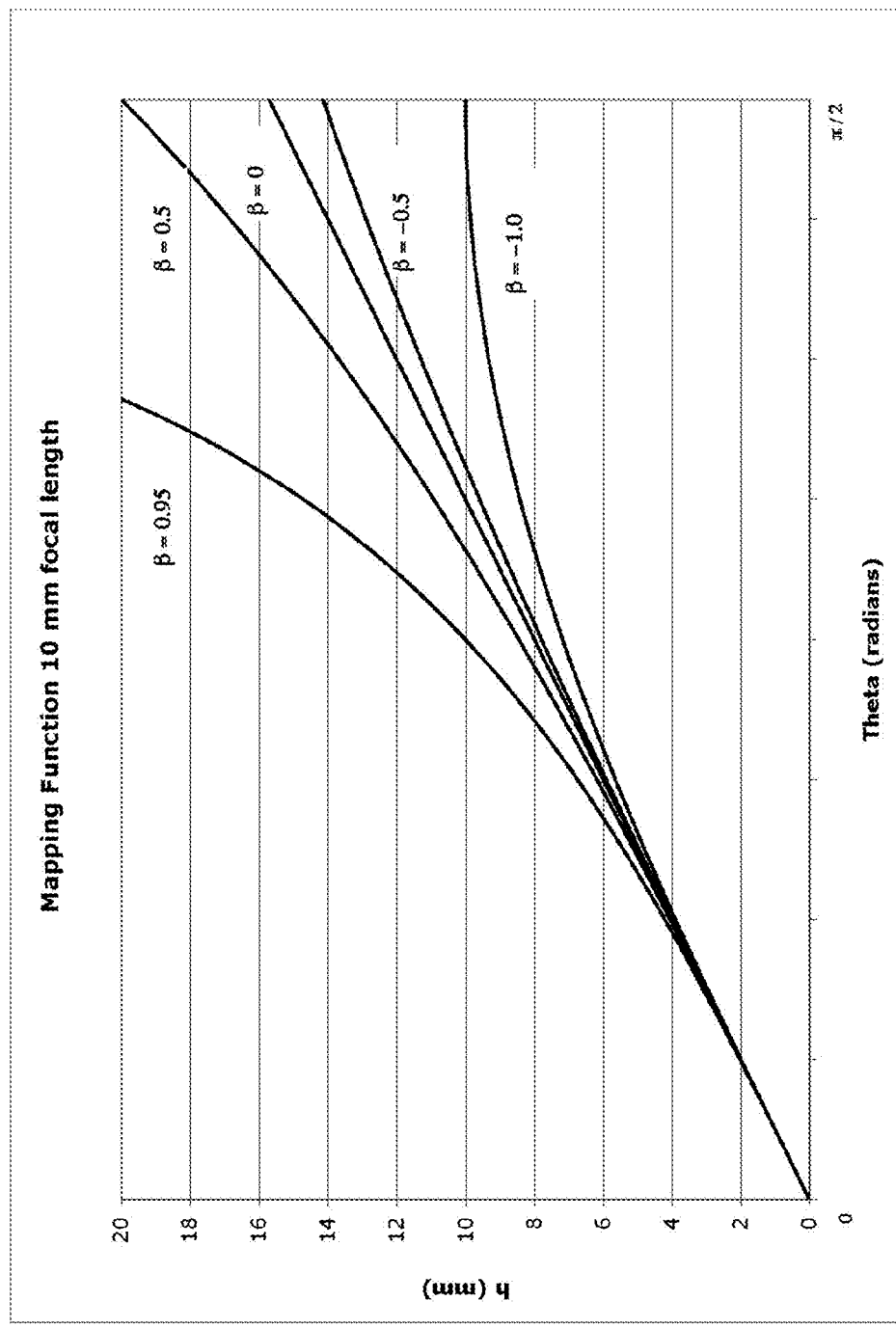
FIG. 2 is a graph of lens mapping functions

Considering FIG. 2, which shows a series of mapping functions for a 10 mm focal length lens with different values of β. Using the f-θ lens as a baseline reference, labeled β=0, most commercially available wide-angle lenses "squeeze" the off-axis objects even more. Their β values are negative. Increasing the value of β provides a lens that has less distortion. A theoretical distortion free lens has a β value of 1.

In one embodiment, the lens mapping function is used in a processing algorithm to process or transform the electronic image formed by the lens and image sensors on its focal plane into a new image without discarding or losing image information in any part of the image. The entire field of view of the lens is still visible after transformation. The image formed by the lens on the image sensor is digitized into an array of points known as pixels. Each pixel will have a pair of coordinates (xx,yy) and a value which measures the light intensity hitting the pixel. For color imagers, the pixel value is represented by a vector with three components (R, G, B). Each component represents the intensity of each primary color.

The pixel coordinates (xx,yy) is a pair of indices identifying the location of the pixel within the electronic imager array. For example, a VGA imager has 640 rows and 480 columns of pixels. For ease of discussion, we will use the center of the array as the origin. If a pixel has coordinates (+100, +100), it means that this pixel is located at the interception of the +100th rows and the +100th columns from center. We will further assume that the optic axis of the lens goes through the center of the imager.

The processing algorithm takes the input image (the source image) captured by the electronic imager, and generates a new image (the target image). We will use (x, y) to represent the pixel coordinates on the target image, and (xx, yy) to present the pixel coordinates on the source image. For each (x, y) pair, the algorithm calculates a corresponding (xx, yy) such as the pixel value at (x,y) on the target image is copied from the pixel value at (xx, yy) on the source image. Using the lens mapping function various useful transformations of the image are possible. Each discussed in turn below.

In one embodiment, an image ("source image") taken with lens1 having rectilinearity β1 and focal length f1 is transformed into a new image ("target image") taken with a hypothetical lens2 having β2 and f2. To keep the same overall horizontal field of view, the f2 and β2 are not two independent variables. They are related to the horizontal field of view (HFOV) via the following equations (derived from Eq (4a) and (4b)):

$$f2 = (H*\beta2)/\tan(\beta2*HFOV/2) \text{ for } \beta2>0 \quad (5a)$$

$$f2 = (H*\beta2)/\sin(\beta2*HFOV/2) \text{ for } \beta2<0 \quad (5b)$$

where H is the image height (half horizontal width of the image size). This equation represents the trade-offs between the focal length and the distortion of a wide-angle lens for a fixed horizontal field of view.

Figure 3:
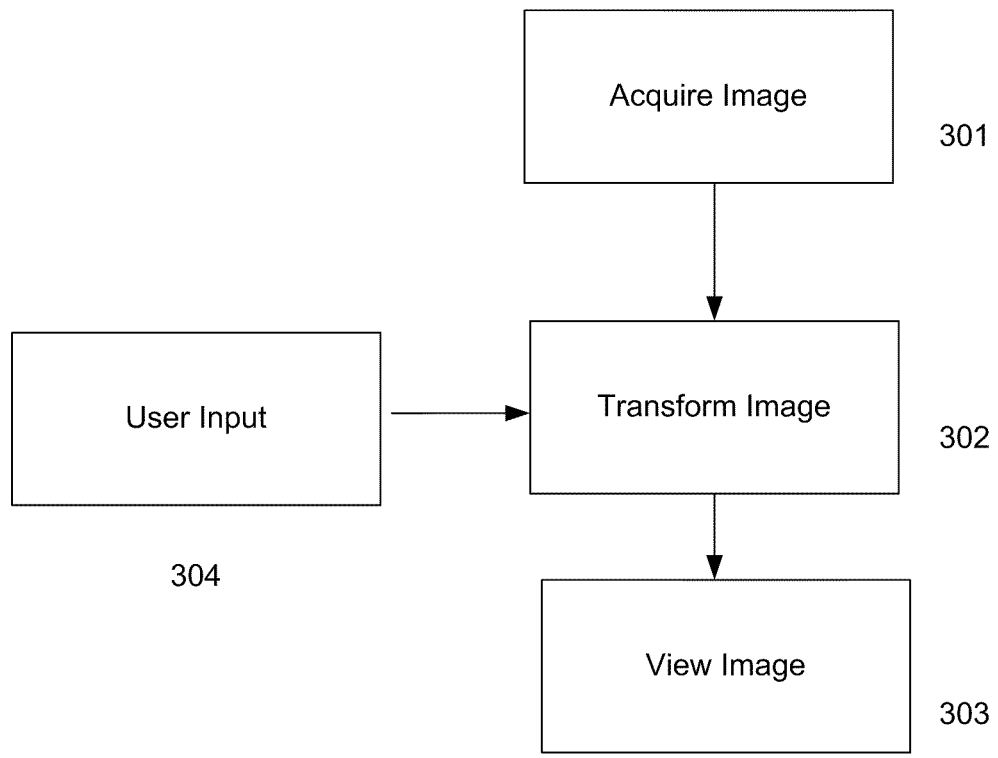
FIG. 3 is a general flow chart for image transformations.

The processing steps shown in FIG. 3 are as follows. An image is acquired 301 using a lens system and an imaging sensor. Nonlimiting examples of the imaging system include a surveillance system, a digital camera, an automotive imaging system such as a backup camera and a medical device such as an endoscope. The image will have a defined set of image parameters 305 including focal length and beta of the imaging system, $f_1$ and $\beta_1$ and the inherent horizontal field of view $HFOV_1$ and image size $w_1$. The image is then transformed 302 using one of several algorithms described below. The transformation step can also be thought of as a filter step prior to viewing the 303, in one default mode the acquired is passed through the transformation step directly. i.e. no transformation is done and the viewed image 303 is the same as the raw acquired image 301.

In another embodiment the operator may decide that a different or transformed image is more appropriate to the purpose or task. The user selects and enters a new set of image parameters 304 that are used to transform the image 302 for viewing 303. The user parameters may be a selection of which of the several transformations described below are to be used. In another embodiment, the user provides parameters that are used along with equations 4 and 5 above to produce a transformed image 303. Once the image is used the user may select a different set of parameters 304 and iteratively determine the best set of parameters to manipulate the image based upon the particular application. Nonlimiting examples of means to select the parameters 304 include keyboard entry, thumbwheels, sliders or any of a variety of user inputs known in the art. In another embodiment the parameters are selected through an automated system. View image may be a computer view of the image that then automatically selects parameters 304 to modify the image to match a preselected set of conditions. In one embodiment the imaging system is integrated into a surveillance system. The automated selection of transform parameters 304 may be selected on the basis of activity or motion detected in a region of the image.

Fixed Field of View Zoom Transformation.

In one embodiment an image taken with an imaging system including a lens with a focal length $f_1$ and a rectilinearity parameter $\beta_1$ is transformed into an image that would be viewed if the image were acquired with a lens having a different rectilinearity $\beta_2$ or with a different focal length $f_2$. This is a fixed field of view transformation.

In this embodiment, the details of the transformation are as follows:
1. For each coordinate point (x,y) in the transformed image, calculate the radial distance to the center of the image, $r = \sqrt{x^2 + y^2}$ 2. Input focal length f2 in pixel units or calculate f2 using Eq (5a) or (5b) with $\beta_2$ and h=X/2, where X is the width of the target image
3. Calculate field angle θ by reversing Eq (4a) or (4b) with $\beta_2$ by setting h=r.
4. Focal length f1 in pixel units is known or calculated using Eq (5a) or (5b) with $\beta_1$ by setting θ=hfov/2 and h=X/2, where hfov is the horizontal field of view, and X is the width of the source image
5. From θ, calculate radial distance h by using Eq (4a) or (4b) with $\beta_1$
6. Determine the source pixel coordinates:
   a. xx=h*x/r or x if only y is to be transformed
   b. yy=h*y/r or y if only x is to be transformed.
7. Set target pixel value at (x, y) to the source pixel value at (xx,yy) for all components.
8. Repeat from beginning for all (x, y) in the target image.

Note that the transformation may be selectively along the x coordinates, the y coordinates or both. Non limiting examples of means to implement the embodiment include:

Use a general purpose computer. The input image (a video frame) is captured and stored into a memory buffer. The output image is generated based on the process using data from the memory buffer.

Use a DSP (a digital signal processor made by companies such as TI and Analog Devices). The DSP chip can be located on the camera board eliminating the need for a separate PC.

Use a FPGA (field programmable gate array made by companies such as Xilinx or Altera). FPGA is a parallel processor allowing real-time performance at high resolution and high frame rate. Once the design is final, an ASIC (application specific integrated circuit) can also be custom fabricated. See article "Distortion correction for a wide-angle lens based on real-time digital image processing" by Jie Jiang, et all, Optical Engineering, Vol 42 No 7, July 2003 Page 2029-2039, incorporated by reference.

Figure 4:
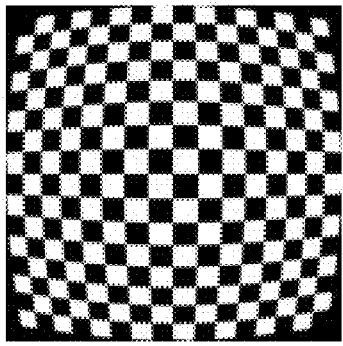
FIG. 4 shows exemplary transformations.
Figure 4:
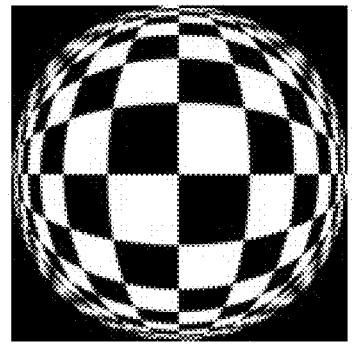
Figure 4:
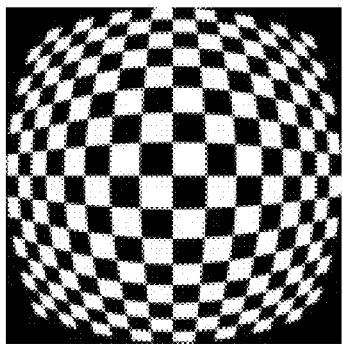
Figure 4:
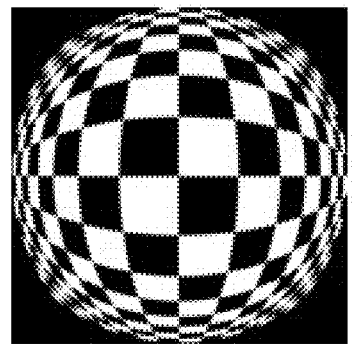
Figure 4:
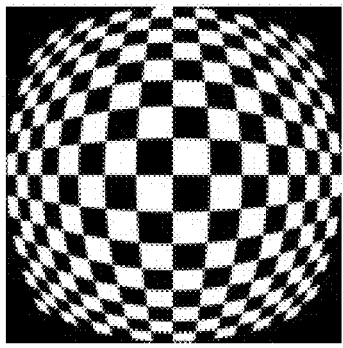
Figure 4:
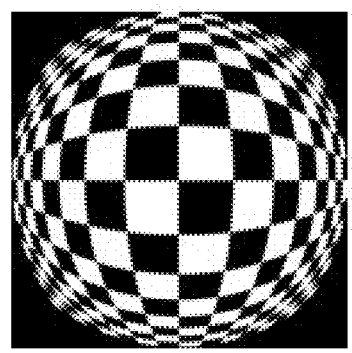
Figure 4:
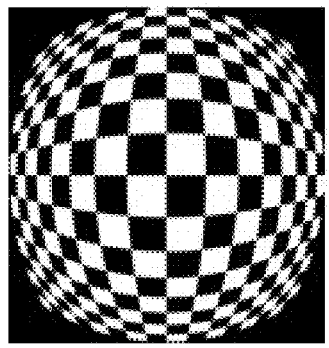

Considering FIG. 4, examples of image transformations in which both x and y coordinates are transformed and the zoom is changed both positively and negatively while maintaining the overall field of view using the algorithm as described above and the lens mapping functions embodied in equations 4 and 5 are shown. The initial image, $\beta_1$=0.67 was taken with a lens having 150 deg horizontal field of view, and a focal length of 6.5 mm. The object is a checker board with black and white squares. The remaining images in FIG. 4 were generated using a programmed algorithm of an embodiment running on a personal computer. The transformations were both of decreased zoom, $\beta_2$=0.77, 0.83 and 0.95 and increased zoom, $\beta_2$=0.20, −0.50 and −0.95. In each case all data is still available in the image. The zoom has been changed while maintaining the field of view. The images represent a simulated image of what would have been taken using a different lens than that actually used. For example the image labeled $\beta_2$=0.20, is a transformation of an image taken with a 6.5 mm lens with a β of +0.67 to an image of a simulated lens with $\beta_2$=0.20 and a focal length of 8.7 mm. The focal length of the simulated lens is fixed by the selection of $\beta_2$ and the requirement that the field of view be maintained. A user could equivalently select a focal length of 8.7 mm and a fixed field of view, which would imply $\beta_2$ would be constrained to 0.20 per equation 5.

Distortion Transformation

In another embodiment an initially acquired image ("source image") taken with lens1 having rectilinearity β1 and focal length f1 is transformed into a new image ("target image") that after transformation appears as if taken with lens2 having β2 and f2. This is a distortion transformation. If β2>β1, the amount of distortion is reduced going from source image to target image. If β2<β1, the amount of distortion is increased in going from source image to target image. The processing steps are as follows:

1. For each (x,y), calculate the radial distance to the center of the image, $r=sqrt(x^2+y^2)$
2. Input the target focal length f2 in pixel units or calculated using Eq (4a) or (4b) with β2 by setting θ=hfov/2 and h=X/2, where hfov is the horizontal field of view of the target image, and X is the width of the target image and Calculate field angle θ by reversing Eq (4a) or (4b) with β2 by setting h=r.
3. Input Focal length f1 in pixel units or calculate $f_1$ using Eq (4a) or (4b) with β1 by setting θ=hfov/2 and h=X/2, where hfov is the horizontal field of view of the source image, and X is the width of the source image, and using θ, calculated in the previous step, calculate radial distance h by using Eq (4a) or (4b) with β1.
4. Determine the source pixel coordinates:
    a. xx=h*x/r or x if only y is to be transformed
    b. yy=h*y/r or y if only x is to be transformed.
5. Set target pixel value at (x, y) to the source pixel value at (xx,yy) for all components (R, G, B).
6. Repeat from step 1 for all (x, y) in the target image.

If b2=1, we are transforming the image into a distortion-free image. In a distortion transformation the field of view is not necessarily preserved. The fixed field of view zoom transformation, discussed above, is a special case of distortion transformation where the f2 and β2 are constrained by equation (5) to maintain the field of view of the original image.

TV Distortion Correction

Figure 7:
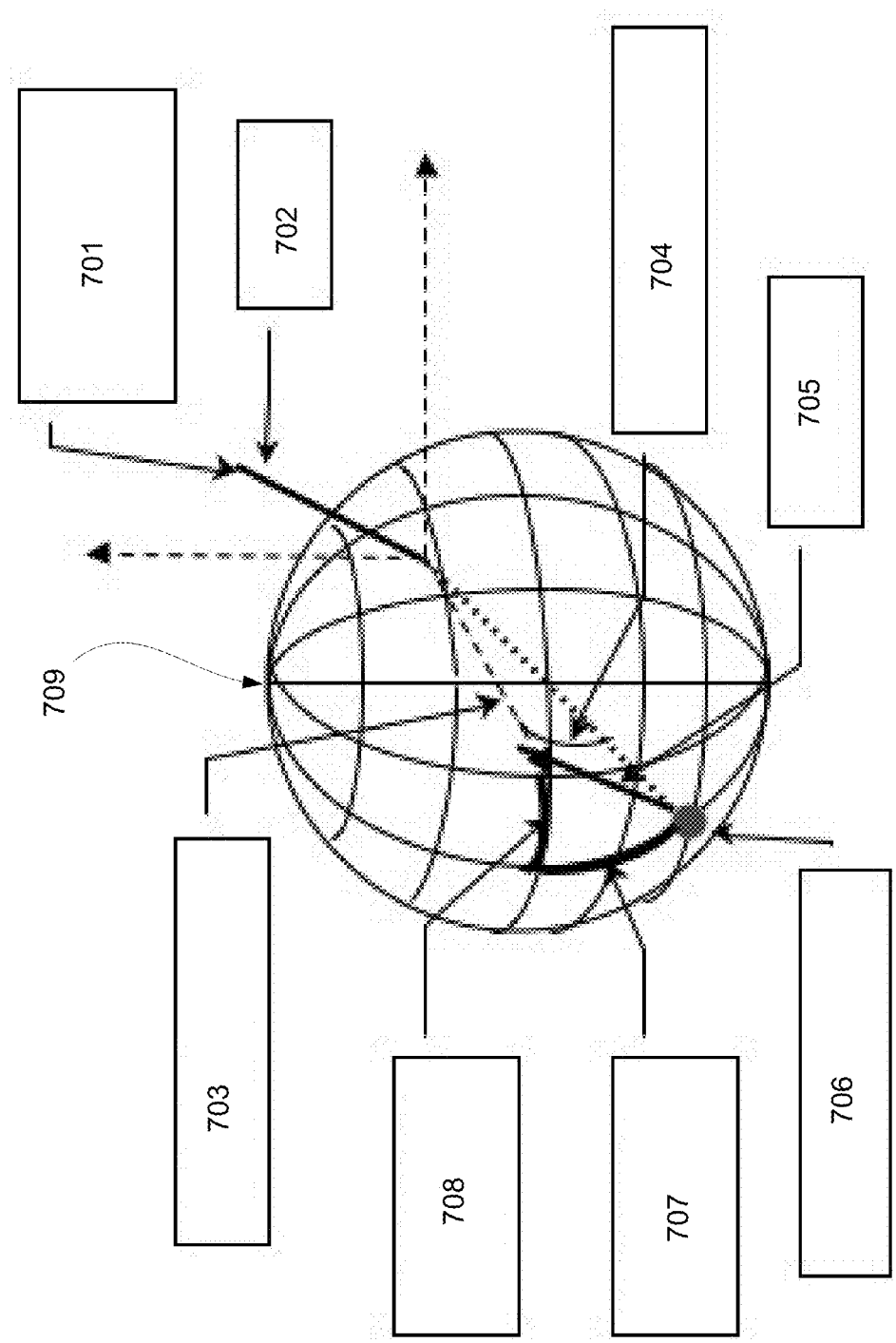
FIG. 7 shows a coordinate system for a spherical transformation.

In another embodiment the off-axis horizontal and vertical lines taken with a lens having $β_1$ and $f_1$ are straightened. The curving of those lines is known as TV distortion. This embodiment is a TV distortion correction. This transformation will accomplish this correction without changing the distance between the horizontal/vertical lines along the y/x axis. The process flow is:

1. User inputs the focal length $f_2$ in pixel units or it is calculated using Eq (4a) or (4b) with $β_2$ by setting θ=hfov/2 and h=X/2, where hfov is the horizontal field of view, and X is the width of the target image.
2. For each (x,y), calculate $θ_x$ by reversing Eq (4a) or (4b) by setting h=x and calculate $θ_y$ by reversing Eq (4a) or (4b) by setting h=y.
3. Compute $θ_d=arctan(sqrt(tan^2(θ_x)+tan^2(θ_y)))$.
4. User inputs focal length $f_1$ in pixel units or calculated using Eq (4a) or (4b) with $β_1$ by setting θ=hfov/2 and h=X/2, where hfov is the horizontal field of view, and X is the width of the source image.
5. Calculate new radial distance h by using Eq (4a) or (4b) and by setting $θ=θ_d$, calculated above.
6. Calculate the source pixel coordinates:
    a. $xx=h*tan(θ_x)/tan(θ_d)$ or x if only y is to be transformed
    b. $yy=h*tan(θ_y)/tan(θ_d)$ or y if only x is to be transformed.
7. Set target pixel value at (x, y) to the source pixel value at (xx,yy) for all components.
8. Repeat from step 2 for all (x, y) in the target image Spherical Projection In another embodiment the acquired image is transformed through a spherical projection. Referring to FIG. 7, each source image point 701 with coordinates (xx, yy) and distance h(θ) 702 from the origin, is projected onto a spherical object surface 709 with unity radius centered on the lens pupil. The corresponding target image point 706 is the projected image formed on the object surface with the x coordinate being the longitudinal angle γ 708, and the y the latitudinal angle ϕ 707 on the object surface. The optic axis 703 goes through the equator. For a pixel 706 with coordinate (x, y) on the target image, the corresponding longitudinal angle γ and latitudinal angle ϕ are:

$$γ=x/X*hfov \quad (6a)$$

$$ϕ=y/X*hfov \quad (6b)$$

Where X is the width and hfov is the horizontal field of view of the target image.

The distance to the optic-axis 705 (perpendicular to the axis) from this pixel is then:

$$d=sqrt(sin^2(γ)*cos^2(ϕ)+sin^2(ϕ)) \quad (7a)$$

From this, we can derive the field angle 704 for this pixel:

$$θ=arcsin(d) \quad (7b)$$

We can now apply Eq (4a) and (4b) to compute the image height h on the source image for the same incident angle θ. The source pixel coordinate (xx, yy) can then be calculated as:

$$xx=h(θ)*sin(γ)*cos(ϕ)/d \quad (8a)$$

$$yy=h(θ)*sin(ϕ)/d \quad (8b)$$

The process steps for this calculation is:
1. Normalize the angles such that it reaches the hfov at full width, and For each (x,y), calculate longitudinal and latitudinal angle per equation (6a) and (6b).
2. Compute:

$$d=sqrt(sin^2(γ)*cos^2(ϕ)+sin^2(ϕ))$$

$$θ=arcsin(d)$$

3. User inputs focal length f1 in pixel units or it is calculated using Eq (4a) or (4b) with β by setting θ=hfov/2 and h=X/2, where hfov is the horizontal field of view, and X is the width of the source image and calculate new radial distance h by using Eq (5a) or (5b).
4. The source pixel coordinates are calculated:
    a) $xx=h(θ)*sin(γ)*cos(ϕ)/d$ or xx=x, if only y is to be transformed
    b) $yy=h(θ)*sin(ϕ)/d$ or yy=y, if only x is to be transformed.
5. Set target pixel value at (x, y) to the source pixel value at (xx,yy) for all components.
6. Repeat from step 1 for all (x, y) in the target image.

Cylindrical Projection

Figure 8:
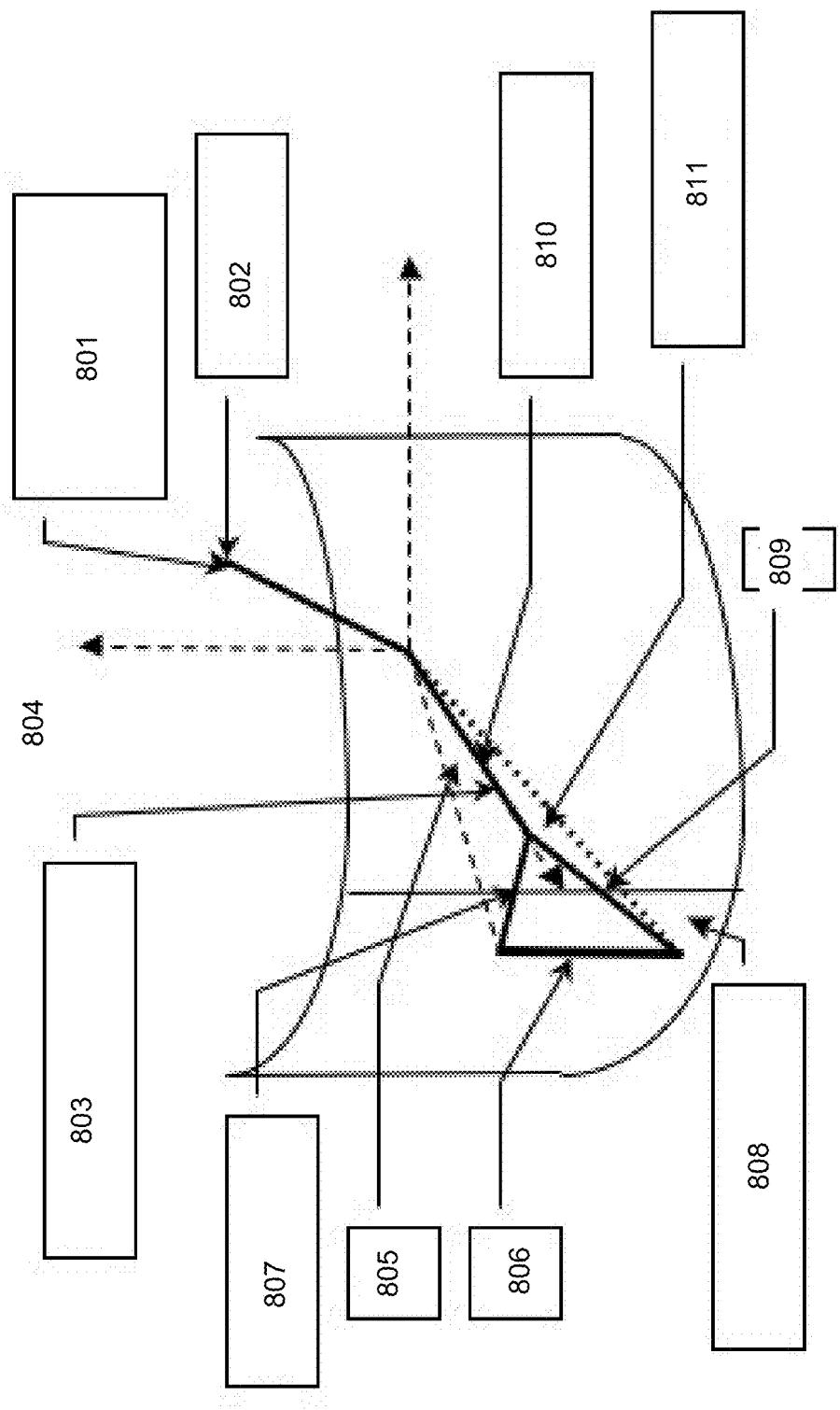
FIG. 8 shows a coordinate system for a cylindrical transformation.

In another embodiment the transformed object surface is a cylinder instead of a sphere, centered on the lens pupil. This is a cylindrical projection shown in FIG. 8. A source pixel 801 with coordinates (xx, yy) defined by h 802 and θ 811, is transformed to a target pixel 808 located on the cylinder surface 804. As in the previous transformation, the x coordinate is still given by the longitudinal angle 805 along the cylindrical surface perpendicular to the cylinder axis. The y coordinate 806 is now the physical height on the cylinder along cylinder axis. The radius of cylinder R is given by normalizing the target image width to the horizontal field of view:

$$R=X/hfov \quad (9a)$$

For a target transformed pixel 808 with coordinates (x, y), the longitudinal angle 805 is then:

$$\gamma = x/R \qquad (9b)$$

The distance d 809 to the optic axis 803 is:

$$d = \sqrt{R^2 \sin^2(\gamma) + y^2} \qquad (9c)$$

The field angle θ 811 for this pixel is then:

$$\theta = a\tan(d/(R \cos(\gamma))) \qquad (9d)$$

Once θ is known, the source pixel coordinate (xx, yy) can be derived using as follows:

$$xx = h(\theta) \cdot R \cdot \sin(\gamma)/d \qquad (10a)$$

$$yy = h(\theta) \cdot y/d \qquad (10b)$$

where h(θ) is from Eq (4a) or (4b). The processing steps for this transformation are:
1. Calculate the radius of cylinder: R=X/hfov and For each (x,y), calculate longitudinal angle γ=x/R.
2. Compute:

a. $d = \sqrt{R^2 \sin^2(\gamma) + y^2}$ b. $\theta = a\tan(d/(R \cos(\gamma)))$ 3. User inputs the focal length f1 in pixel units or it is calculated using Eq (4a) or (4b) with β by setting θ=hfov/2 and h=X/2, where hfov is the horizontal field of view, and X is the width of the source image and calculate new radial distance h by using Eq (4a) or (4b)
4. The source pixel coordinates are then given by:

a. $xx = h(\theta) \cdot R \cdot \sin(\gamma)/d$ or x if only y is to be transformed b. $yy = h(\theta) \cdot y/d$ or y if only x is to be transformed.

5. Set target pixel value at (x, y) to the source pixel value at (xx,yy) for all components.
6. Repeat from step 1 for all (x, y) in the target image.

Transitional Projection

Figure 9:
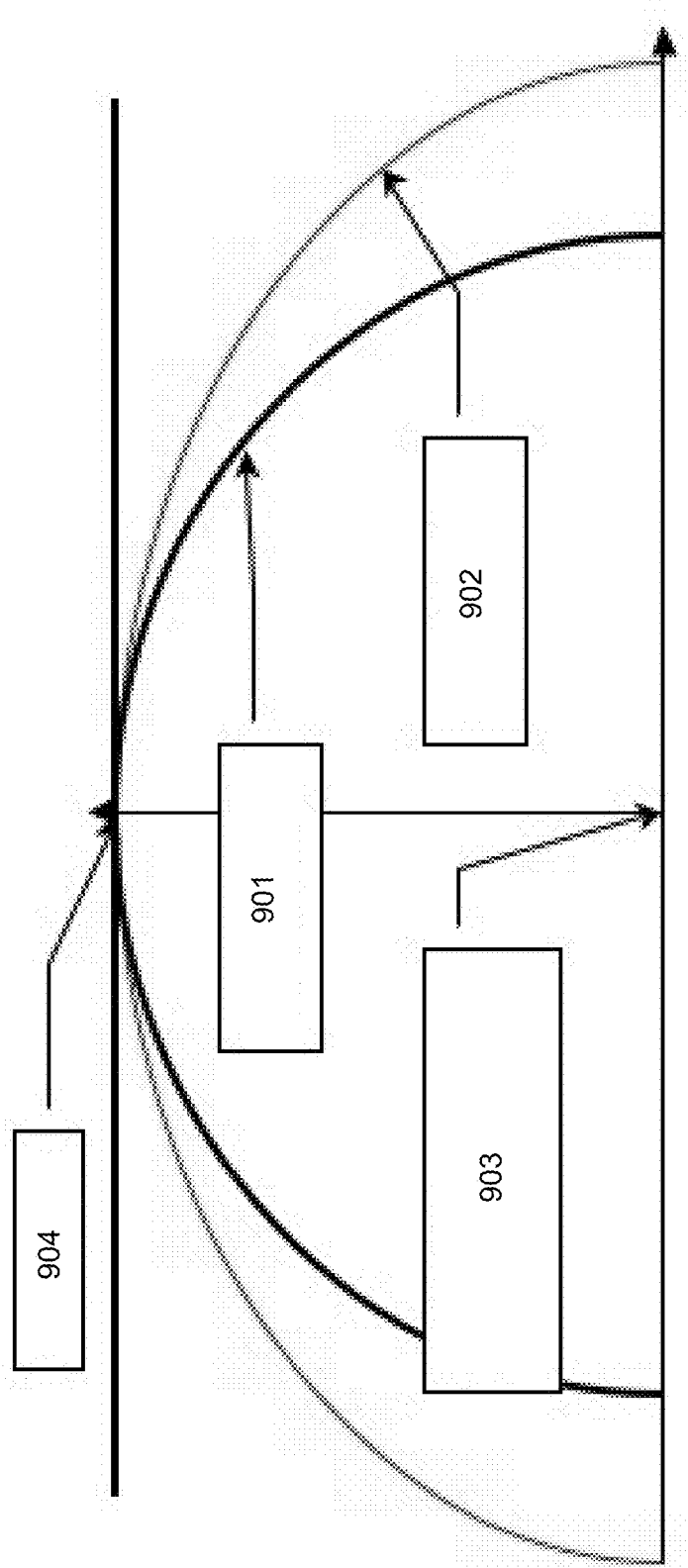
FIG. 9 shows cylindrical and transitional mapping surfaces.

In another embodiment, the object surface is a "flattened" cylinder. This is a transitional projection. Referring to FIG. 9, a cylinder 901 has constant curvature along the axis perpendicular to the cylinder axis. In a transitional projection the projection surface 902 is flattened at the point where the top of the cylinder 904 intercepts the lens optic-axis. The curvature of the object surface increases progressively towards the edge of the object surface. The origin of the projection surface 903 is located at the center of the lens entrance pupil. The horizontal direction (or x direction) is curved while the vertical direction is still straight. With such a transformation, the target image resembles a rectilinear image when the field of view is relatively narrow and it transitions to a panoramic format in a smooth manner as the field of view is increased.

Figure 10:
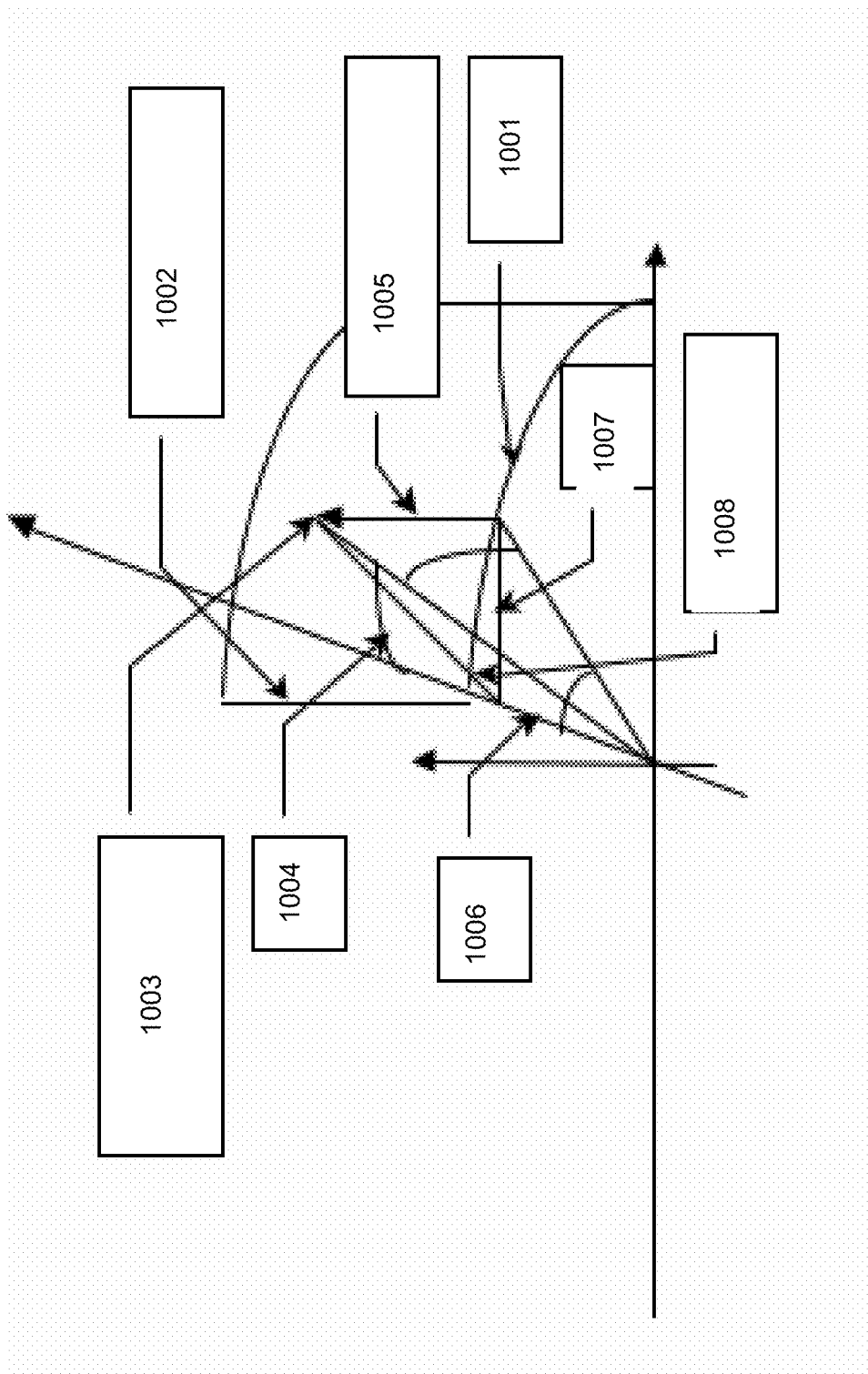
FIG. 10 shows a coordinate system for a transitional transformation.

There are an infinite number of surfaces can be used for transitional projection. A requirement is that it has zero curvature along the vertical axis (y axis) and it curves along the horizontal axis (x axis) in a way such that the curvature is increased progressively when moving away from the center line of the object surface. In FIG. 10, a target pixel location 1003, will have an x and y coordinate defined by: the x coordinate will be the arc length measured from center of the object surface 1002, and y is the height along y axis 1005. In one preferred embodiment (nonlimiting example), the transitional object surface 1001 is a section of cycloid. A cycloid is the line traced by a point on the perimeter of a rolling cylinder.

The parametric equation for a cycloid is as follows:

$$Xc = a \cdot (t - \sin(t)) - a \cdot \pi \qquad (11a)$$

$$Yc = a \cdot (1 - \cos(t)) \qquad (11b)$$

Where a is the radius of the rolling cylinder that generates the cycloid 1001, and parameter t is in the range of 0 to 2π. The arc length as measured from left end point of the cycloid is given as (also in parametric form):

$$S = 8 \cdot a \cdot \sin^2(1/4 \cdot t) - 4 \cdot a \qquad (12)$$

Now imagine that the lens pupil is in the center (Xc=0, Yc=0) of the cycloid, the maximum horizontal field of view is now π. The entire arc length of a cycloid is 8*a from left endpoint (t=0) to right endpoint (t=2π). For exemplary purposes only, we set a=π/8. We will further assume that the target image has a horizontal field of view of HFOV=π to allow us to achieve a closed formed solution. For other HFOV values, one must solve the following equation for t in order to get the te value for the left and right endpoints:

$$Xc(t)/Yc(t) = \tan(\text{HFOV}/2) \qquad (13)$$

Once the left endpoint, $t_e$, value is obtained, the arc length corresponding to the half width of the target image is then:

$$S_e = \pi/2 - \pi \cdot \sin^2(1/4 \cdot t_e) \qquad (14)$$

$S_e$ will be used to normalize the pixel coordinate to the real coordinate on the cycloid surface. The normalization factor N is $2 \cdot S_e/X$ where X is the horizontal width of the target image in pixels. Now refer to FIG. 10, for each pixel with coordinate (x, y) where x is the arc length measured from the center line of the cycloid, or top 904 in the view of FIG. 9, we perform the following calculations. Solve for t by reversing equation (12):

$$t = 4 \cdot a \sin(\sqrt{(x \cdot N + \pi/2)/\pi}) \qquad (15)$$

Knowing t, we can then calculate the field angle 1004:

$$\theta = a\cos(Y_c/\sqrt{X_c^2 + Y_c^2 + (y \cdot N)^2}) \qquad (16)$$

$$xx = h(\theta) \cdot X_c/\sqrt{X_c^2 + (y \cdot N)^2} \qquad (17a)$$

$$yy = h(\theta) \cdot y \cdot N/\sqrt{X_c^2 + (y \cdot N)^2} \qquad (17b)$$

The calculation process for a transitional projection is:
1. For the target hfov, calculate the horizontal arc length $S_e$ (from object surface center). Compute the normalization factor $N = 2 \cdot S_e/X$ where X is the target image width in pixels and for each (x,y), normalize them to the actual dimension on the object surface by multiplying the normalization factor.
2. Compute the field angle θ as:

a. $\theta = a\cos(Y_c/\sqrt{X_c^2 + Y_c^2 + (y \cdot N)^2})$ b. where $X_c$, $Y_c$ and (y*N) are the coordinates of the target pixel relative to the origin of the transformation object surface 3. Calculate the radial distance h by using the lens mapping function, equation 4. Normalize the mapping function, such that at the source hfov/2, the image height is X/2 where X is the source image width.
4. Calculate the source pixel coordinates:

a. $xx = h(\theta) \cdot X_c/\sqrt{X_c^2 + (y \cdot N)^2}$ or x if only y is to be transformed b. $yy = h(\theta) \cdot y \cdot N/\sqrt{X_c^2 + (y \cdot N)^2}$ or y if only x is to be transformed 5. Set target pixel value at (x, y) to the source pixel value at (xx,yy) for all components.

Repeat from step 1 for all (x, y) in the target image.

Hardware Examples

Figure 5:
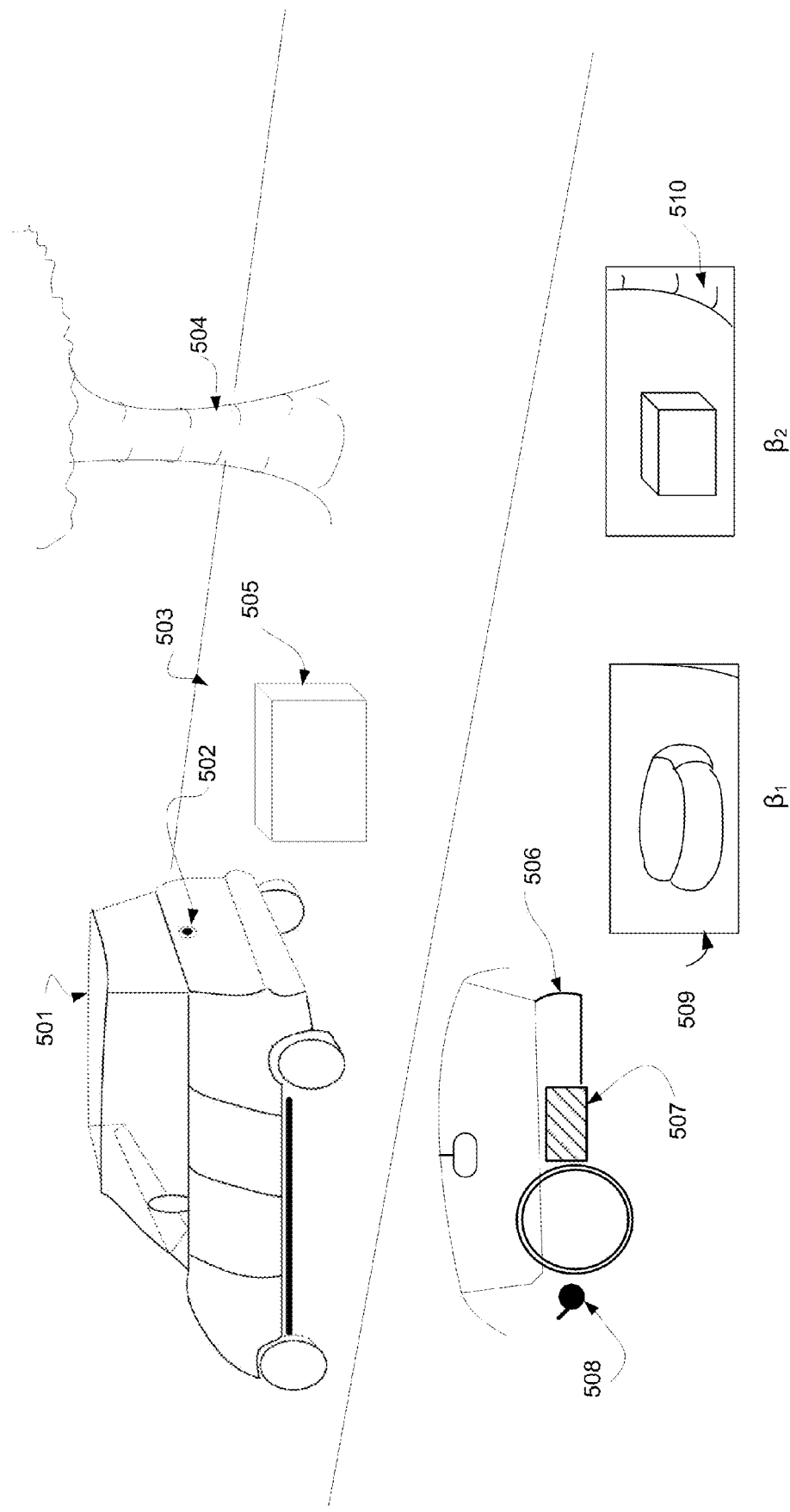
FIG. 5 shows an automotive embodiment.

In another embodiment shown in FIG. 5, a vehicle 501 is fitted with an imaging system including a camera fit with a lens 502. The vehicle may be traveling along a path 503 in which there are obstacles such as a tree 504 or a box 505. The imaging system further includes a display screen 507 fit in the dashboard of the vehicle 506. The viewing system further includes a means to adjust the image, here shown as a knob 508. The display screen presents an image 509 of the objects that are, in the example shown, behind the vehicle. The imaging system acquires an image that is characteristic of the physical components (lens, sensor, etc) of the imaging system. The original image provides a view that is reflective of the image data taken using a lens with a characteristic $f_1$ and $\beta_1$ and an imaging sensor of a given size. The original image may provide a view of the objects 504, 505 as shown in image 509. In one embodiment the knob 508 is turned and electronically select a value for $f_2$ and/or $\beta_2$. The imaging system further includes a processor that transforms the original image 509 into the image 510 through use of the algorithms as discussed above. If $f_2$ and $\beta_2$ are constrained by equation 5 the field of view in FIGS. 509 and 510 are identical, however as seen the relative visibility of objects 504 and 505 is changed from one view to the next. Additional non-limiting exemplary vehicular embodiments include backup warning, automatic parking and collision avoidance.

In another embodiment non-limiting exemplary means to select $f_2$ and/or $\beta_2$ include a slider, a thumbwheel, a button or other user interface means known in the art. In other embodiments the camera 502 may be at other locations on the vehicle, the display 507 may be located outside of the dashboard of the vehicle and the control means 508 may be any of the user interfaces discussed above and located at other locations for example on the steering wheel of the vehicle.

Figure 6:
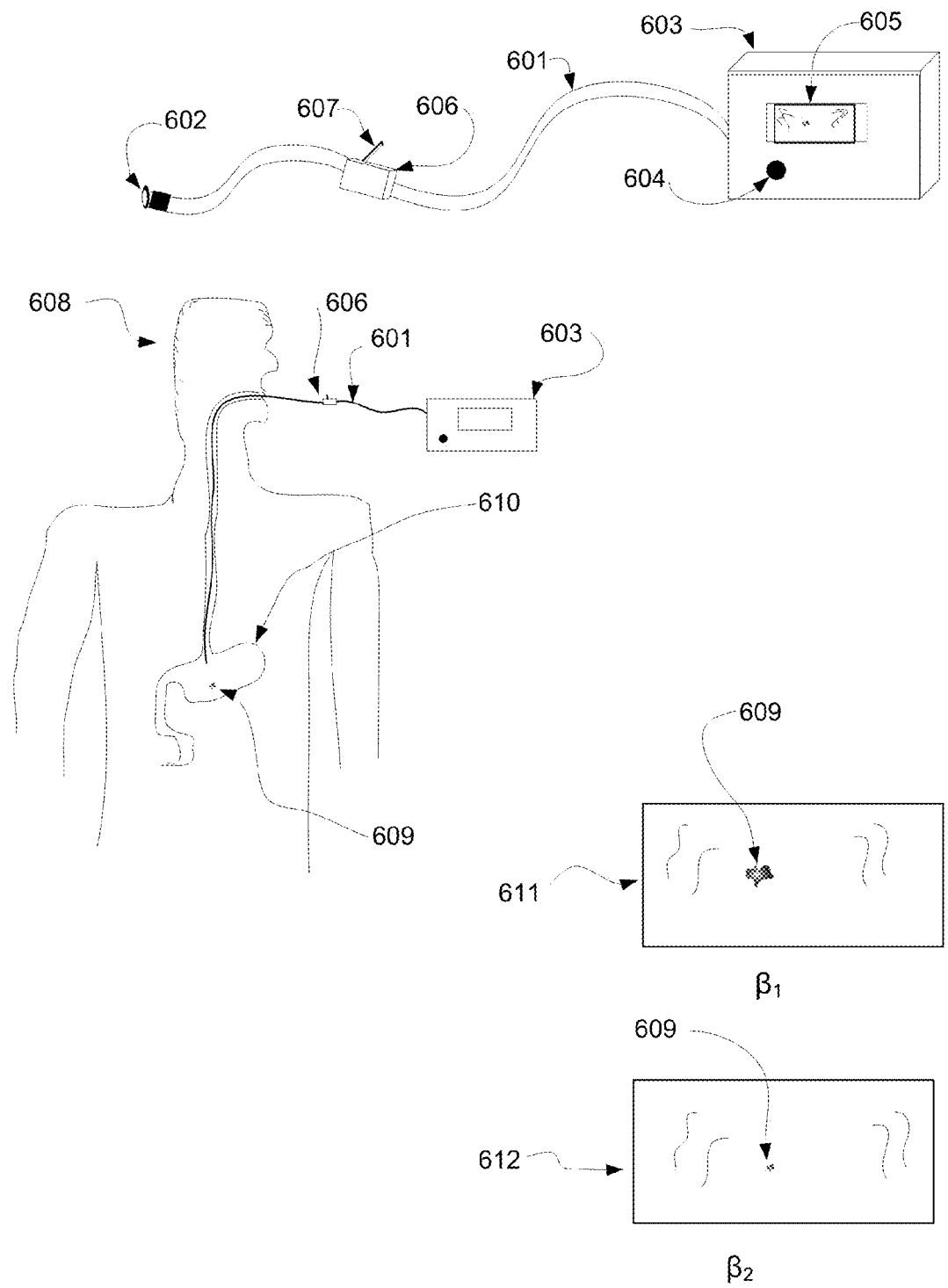
FIG. 6 shows an endoscopic embodiment.

In another embodiment shown in FIG. 6, an endoscope is comprised of an imaging lens 602 connected via an optical fiber or electrical line 601 to a controller 603. The endoscope further includes an imaging sensor that may be incorporated near the lens 602 or may be in the controller 603 in which case the connecting line 601 is fiber optic. The controller further includes a display 605 for viewing images captured through the imaging lens 602 and an adjusting means 604 to adjust parameters for the display. In use the lens is inserted into the patient 608. In this case the endoscope is one designed for use in viewing the patient's digestive tract. The exemplary use is to view the inside of the patient's stomach 610 and in particular see an ulcer 609 in the stomach wall. In one embodiment, the endoscope further includes a hand held connector 606 that includes an adjustment means 607 for adjusting the image data captured by the lens 602 and sensor. The original image reflects the physical parameters of the imaging system include the focal length and rectilinearity parameter of the lens $f_1$ and $\beta_1$ and the size of the imaging sensor. The original image may provide a view of the object 609 as shown in image 611. In one embodiment the adjustment means 604 or 607 is turned and electronically selects a value for $f_2$ and/or $\beta_2$. The imaging system further includes a processor that transforms the original image 611 into the image 612 through use of the algorithms as discussed above. If $f_2$ and $\beta_2$ are constrained by equation 5 the field of view in FIGS. 611 and 612 are identical, however as seen the relative visibility of object 609 is changed from one view to the next. In one view 611 the doctor or practitioner may obtain a close view of a defect 609. In another view 612 the doctor or practitioner can view both the defect 609 and the condition of the surrounding tissue. In another embodiment non-limiting exemplary means to select $f_2$ and/or $\beta_2$ include a slider, a thumbwheel, a button or other user interface means known in the art. The discussion of a gastro-intestinal endoscope is for exemplary purposes, embodiments of the invention would apply equally well to other endoscope and borescope systems known in the art. Nonlimiting examples include brachioscopes, angioscopes, colonscopes, laparoscope and arthroscopes.

Figure 11:
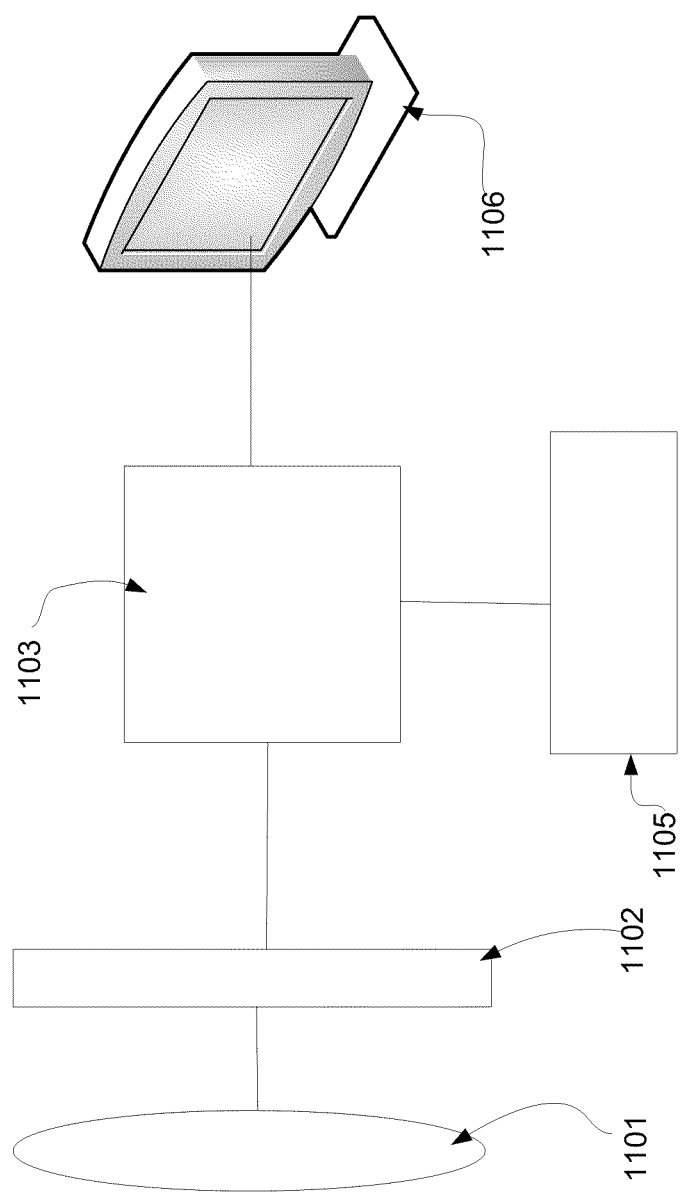
FIG. 11 shows a diagram of a typical imaging system for practicing the invention.

Referring to FIG. 11, a typical image acquisition and processor system for practicing the invention is shown, which comprises lens 1101, image sensor 1102, digital signal processor 1103, which accepts instructions from a user interface 1105 and produces transformed and corrected images on a display 1106. Digital signal processor 1103 is the primary digital interface with the image sensor and includes sufficient buffer memory to allow images to be acquired rapidly. The digital signal processor also takes in the image sensor data and performs various image correction and transformation operations to develop the desired image on the display device 1106 for which nonlimiting exemplary embodiments include an LCD screen, display goggles, and a "heads up" display. In an alternative embodiment, not shown, he processor for image acquisition is separate from the processor used to manipulate and display the image. In another embodiment the processor for display and manipulating the image may be located remotely from the location of the image acquisition process. In another embodiment processor 1103 and image sensor 1102 form an integral part such one integrated circuit.

Other nonlimiting exemplary embodiments of the imaging system shown in FIG. 11 include a camera for obtaining digital photographs, a surveillance system for security applications, and environmental displays used in vehicle training simulators, reality based games, and the control of remotely controlled vehicles. The imaging system comprises a lens characterized by a mapping function as shown in Equation 4, described elsewhere in this application. In a preferred embodiment, the wide-angle lens is selected from:
  a. 6 element wide angle lens (FIG. 12)
  b. 7 element wide angle lens (FIG. 13)
and the processor is programmed to transform the acquired image using at least one of the transformations selected from:
  1. Distortion Transformation (with fixed field of view zoom as a special case).
  2. TV distortion correction
  3. Spherical transformation (FIG. 7)
  4. Cylindrical Transformation (FIG. 8)
  5. Transitional Transformation (FIGS. 9, 10)

Lens Systems

In another embodiment lenses are described that are especially suitable for use in an imaging system that will make use of the aforementioned transformations. The lenses are designed such that the lens mapping function can be characterized sufficiently by equations 4a) and 4b). This constraint along with the other design parameters of physical size of the lens, number of lens elements and field of view when entered into a design program such as Code V marketed by Optical Research Associates in Pasadena, Calif. and Zemax marketed by Zemax Corporation in Bellevue, Wash. will result in a prescription for a lens such as that shown in FIGS. 12 and 13 and further described in Table 1 discussed below. Note in the context of this application "prescription" refers to the detailed design parameters that define a lens system and do not refer to the medical or ophthalmic definition of a prescribed lens to correct a users vision.

Figure 12:
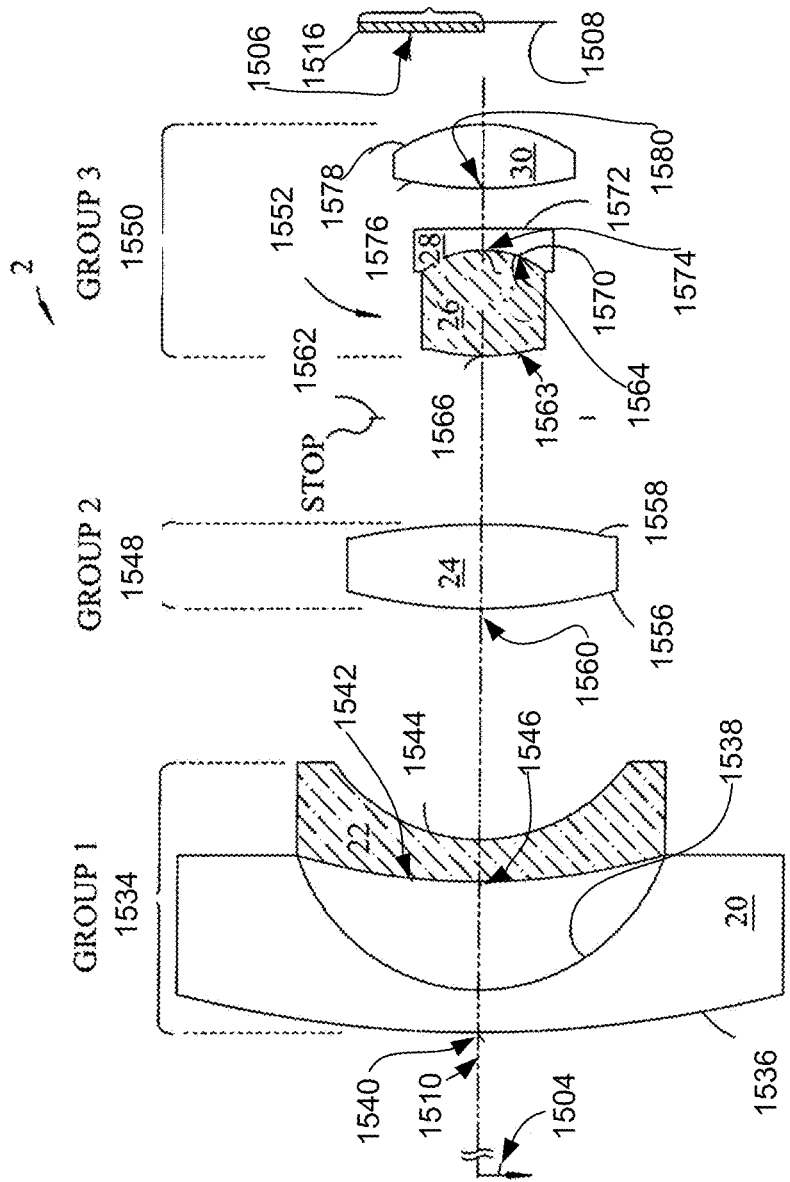
FIG. 12 is a schematic side sectional view of a first embodiment of an—objective lens with three groups of lenses divided into six elements.
Figure 13:
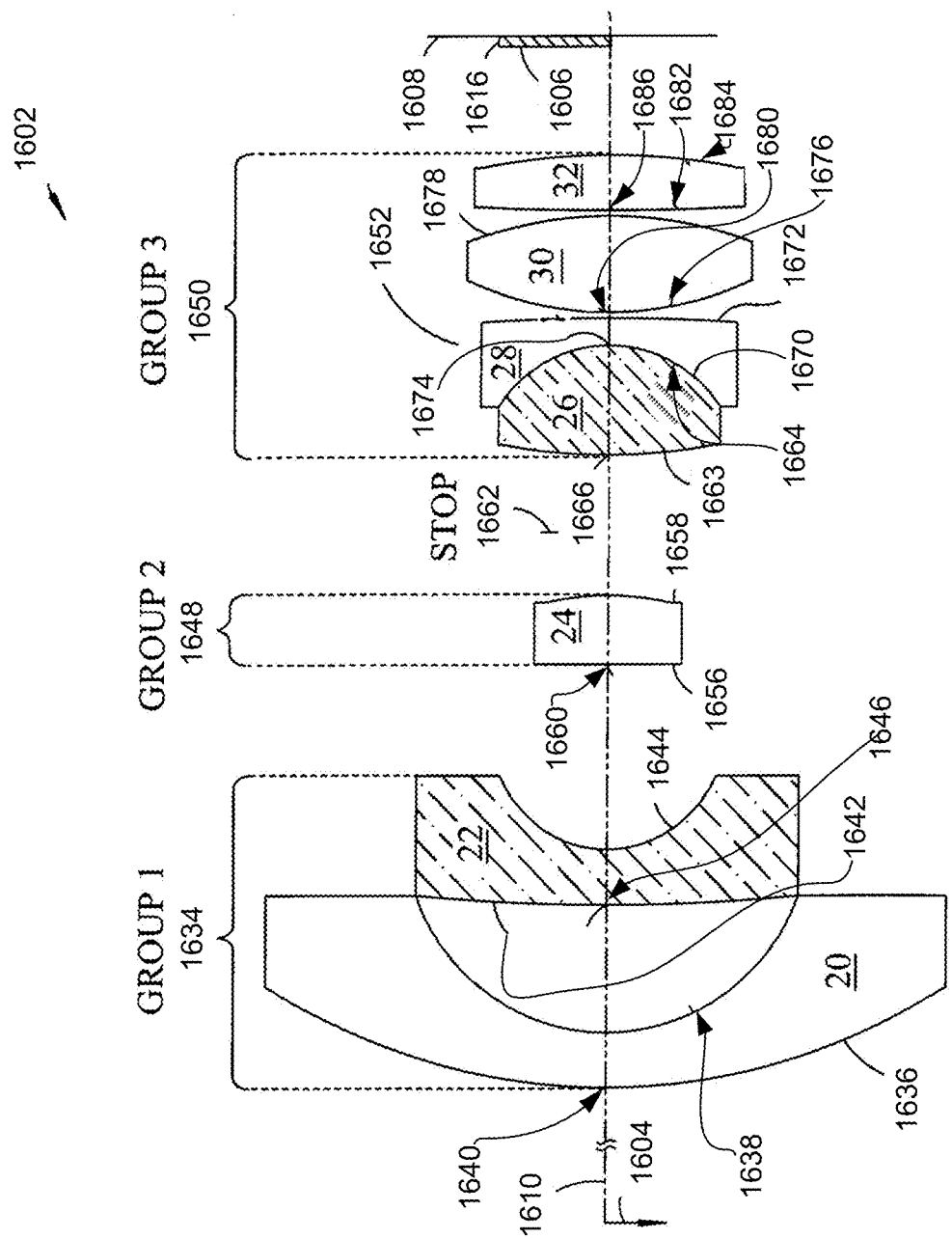
FIG. 13 is a schematic side sectional view of a second embodiment of an—objective lens with three groups of lenses divided into seven elements.

Embodiments of lens systems that may be used in this invention are described in the two alternative designs shown in FIGS. 12-13. Both systems follow the lens mapping function equations 4a) and 4b). The lens elements are arranged into three groups. Group 1, a first group (counting from the object side on the left of FIGS. 15, and 16) has at least two elements. At least one of the two elements is an aspheric element. An aspheric element is a lens element having at least one aspheric surface. The second group with a positive power has a single or multiple lens elements. The second group is labeled "group 2". The third group has a positive optical power, and multiple elements. An aperture stop is positioned between group 2 and group 3. All lens groups and the aperture stop are coaxially aligned on a common optical axis.

FIG. 12 shows an embodiment of the wide angle objective lens with three lens groups that have a total of six lens elements. This is a 6-element wide angle lens. The third lens group includes doublet 1552 with a fourth and fifth lens elements 26, 28 and a sixth lens element 30 FIG. 13 shows an embodiment of the—wide angle objective lens in which the third lens group 1650, group 3, includes the doublet 1652 with a fourth and fifth lens elements 26, 28, a sixth lens element 30 and a seventh lens element 32 which is an aspheric element in preferred embodiments. This is a 7-element-wide angle lens. The description for the group 1 and group 2 topologies of the embodiments of FIGS. 12 and 13 are common.

The embodiments of FIGS. 12 and 13 each show the third lens group (1550, 1650) as including cemented doublet (1552, 1652) having has a first lens element 26 (which is the fourth lens element in the wide angle objective lens), and a second lens element 28 (which is the fifth lens element in the—wide angle objective lens). The first lens element 26 has a convex object surface (1562, 1662) facing the object, a convex image surface (1564, 1664) facing the image plane (1508, 1608) and a vertex (1566, 1666). In each embodiment, the third lens group (1550, 1650) has a positive power.

The second lens element 28 in the doublet (1552, 1652) of the third lens group (1550, 1650) or the fifth lens element of the wide angle objective lens, has a concave object surface (1570, 1670) facing the object (1504, 1604), a convex image surface (1572, 1672) facing the image plane (1508, 1608) and a vertex (1574, 1674). The first and second lens elements 26, 28 are joined with optical cement to form the positively powered cemented doublet (1552, 1652). The term "positively powered" means that the power of the cemented doublet pair (1552, 1652) is greater than zero.

The third lens element 30 has a convex object surface (1576, 1676) facing the object, a convex image surface (1578, 1678) facing the image plane (1508, 1608) and a vertex (1580, 1680).

The third lens element 30 in the third lens group (1550, 1650) has a positive vertex power. In the embodiment of FIG. 12, the third lens element 30 in the third lens group 1550 is an aspheric lens element having a varying power that is positive at the vertex 1580 and that decreases with increasing radial distance from the vertex 1580. For example the power at the vertex 1580 may be +5 diopters decreasing to +4 diopters at the edge of the element.

Performance of the embodiment of FIG. 12 is further improved by the embodiment of FIG. 13 with the addition of a seventh lens element 32 as the fourth lens element 32 in the third lens group 1650. The fourth lens element 32 in the third lens group 1650 has an object surface 1682 facing the object 1604, an image surface 1684 facing the image plane 1608, a vertex 1686, and a positive vertex power. In the improved embodiment of FIG. 13, the fourth lens element 32 in the third lens group 1650 is an aspheric element having a varying power. The power is positive at the vertex 1686 on lens surface 1682, and decreases with increasing radial distance from the vertex 1686. For example, the power at vertex 1686 may be +5 diopters decreasing to +4 diopters at the edge of the element. In FIG. 13, lens element 30 may be an aspheric lens element, or it may be a positive lens element with spherical surfaces. The constraint to follow the lens mapping functions of equations 4a) and 4b) when combined with a set of design parameters such as the focal length, physical dimensions of the lens and the dimensions of the sensor to be used with the lens along with the lens elements selected as shown will result in a recipe for the lens to allow manufacturing of the specific lens.

The prescription for the six element design of FIG. 12 appears in Tables 1 and 2 below. The prescription for the seven element design of FIG. 13 can be similarly determined but is not shown. The prescriptions for the elements and the lens designs for the embodiment of FIGS. 12 and 13 are characterized to provide a level of wide angle performance that also meets the criterion of equations 4a) and 4b).

The embodiments of FIGS. 12 and 13 also provide a very compact lens design with a very short total track length (TTL). The total track length is the distance from the first lens element vertex (1548, 1648) to the image plane (1508, 1608) when the object is at infinity. When the lens elements of the—wide angle objective lens are made to the prescriptions of Table 1 and 2, the performance of the two embodiments of the wide angle objective lens satisfies TTL/f<33, as shown in the title block of Tables 1. The f/# (or "f" number) in the title blocks of Tables 1, is the ratio of the focal length "f" divided by the pupil diameter of the lens assembly.

Aspheric Surfaces

Conventional lens elements are made by grinding and polishing glass lens blanks. The two surfaces of a lens element are typically spherical. However, an aspheric element is a lens element that has at least one of its two surfaces described by a general aspheric equation such as Equation 18

$$z = \frac{cr^2}{1 + \sqrt{1 - (1+k)c^2 r^2}} + \alpha_1 r^2 + \alpha_2 r^4 + \alpha_3 r^6 + \alpha_4 r^8 + \alpha_5 r^{10} + \alpha_6 r^{12} + \alpha_7 r^{14} + \alpha_8 r^{16}.$$

Equation 18 where z is the surface sag relative to the vertex of the lens on the lens surface. n Eq. 18, the variable r is the radial distance from the optical axis. The constant c is the curvature (inverse of radius) at the vertex of the surface. The constant k is a "conic" constant. The other coefficients ($\alpha 1, \alpha 2, \ldots$) are the aspheric coefficients provided in Table 2. The coefficients characterize the depressions in the lens surface that are made by molding the surface to match a modeled mathematical envelope in a suitable glass or plastic material. In the embodiments of FIGS. 12 and 13, surface (1542, 1642) and (1544, 1644) of element 22, surface 1578 of element 30 in the embodiment of FIG. 12, and surface 1684 of element 32 with the embodiment of FIG. 13 are aspheric surfaces described by use of equation 18 above using the coefficients found in Table 2 for the embodiment of FIG. 12. The coefficients for the embodiment of FIG. 13 (not shown) are similarly determined where the constraint of the lens dimensions, f#, lens elements and the requirement to follow lens mapping function equations 4a) and 4b) result in a recipe for the manufacture of the embodiment of FIG. 13.

Explanation of Tables

The Title block at the top of Tables 1 provide the effective focal length f, the f#, the TTL or Total Track Length, the Image Height (h) at the full field angle and the ratio of TTL/f for the Embodiment. The columns of Table 1 are titled for: "Surface", "Type", "Radius", "Thickness", "Index (Nd)", and "Abbe Number". The lens element material is specified by the refractive index and Abbe number. The absence of an "Index" value in a cell in Table 1 signals that the value in the "Thickness" column cell adjacent to the missing value in the Index cell, is the distance to the vertex of the next lens surface. The "Index" column provides the index of refraction for the material at 588 nm. The "Abbe Number" is provided in the rightmost column. The data of Tables 1 and 2 are purposely reported to a limited number of significant digits to protect trade secret information of the inventor. In practice the recipe for the lens would be calculated to a number of significant digits that would be determined by the manufacturing capabilities.

At Table 1, surface 6, the Index Cell is blank. Therefore, the adjacent cell to the left, the "Thickness" column cell, shows the distance to be measured from the image surface of the preceding lens surface to the next surface which is the distance to the STOP. Surface 7, the start of the next row, is the start of the STOP row. Thickness Cell on Row 7 shows the distance from the STOP to vertex (1566, 1666) on the first doublet lens 26. The distance from surface (1558, 1658) on lens element 24 to the STOP is 4 mm. The distance from the STOP to vertex 1566 on surface 1508 is 0.4 mm for the embodiment of FIG. 12.

TABLE 1

SURFACE DATA SUMMARY FOR
6-ELEMENT-WIDE ANGLE LENS

| Surf OBJ | Type | Radius Infinity | Thickness Infinity | Index | Abbe# |
|---|---|---|---|---|---|
| 1 | STANDARD | 30. | 1.00 | 1.8 | 47 |
| 2 | STANDARD | 5 | 3 | | |
| 3 | EVENASPH | −6 | 1 | 1.5 | 56 |
| 4 | EVENASPH | 9 | 5 | | |
| 5 | STANDARD | 13 | 2 | 1.6 | 25 |
| 6 | STANDARD | −16 | 4 | | |
| 7 | STOP | Infinity | .4 | | |
| 8 | STANDARD | 5 | 3 | 1.6 | 60 |
| 9 | STANDARD | −3 | 0.5 | 1.9 | 24 |
| 10 | STANDARD | −70 | 0.9 | | |
| 11 | STANDARD | 10 | 2 | 1.5 | 56 |
| 12 | EVENASPH | −3 | 3 | | |
| IMA | | Infinity | | | |

Focal Length f = 1.25 mm, F# = 2.0, Total track length TTL = 20 mm. h = 2 mm at θ = 70°

TABLE 2

SURFACE DATA DETAILS FOR
6-ELEMENT-WIDE ANGLE LENS
Equation 1 parameters for Aspheric Element
of Example 3

| Surface 3 | |
|---|---|
| Coeff on r 2 : | 0 |
| Coeff on r 4 : | 0.01 |
| Coeff on r 6 : | −0.0002 |
| Coeff on r 8 : | 5.0e−006 |
| Coeff on r 10: | 0 |
| Coeff on r 12: | 0 |
| Coeff on r 14: | 0 |
| Coeff on r 16: | 0 |
| Surface 4 | |
| Coeff on r 2 : | 0 |
| Coeff on r 4 : | 0.004 |
| Coeff on r 6 : | −0.0008 |
| Coeff on r 8 : | −4.0e−005 |
| Coeff on r 10: | 0 |
| Coeff on r 12: | 0 |

TABLE 2-continued

SURFACE DATA DETAILS FOR
6-ELEMENT-WIDE ANGLE LENS
Equation 1 parameters for Aspheric Element
of Example 3

| Coeff on r 14: | 0 |
|---|---|
| Coeff on r 16: | 0 |
| Surface 12 | |
| Coeff on r 2 : | 0 |
| Coeff on r 4 : | 0.002 |
| Coeff on r 6 : | −0.002 |
| Coeff on r 8 : | 0.0004 |
| Coeff on r 10: | 0 |
| Coeff on r 12: | 0 |
| Coeff on r 14: | 0 |
| Coeff on r 16: | 0 |

SUMMARY

An imaging system and method of application, including lens designs tailored to be used with particular transformation algorithms, electronic hardware and algorithms for image transformations is described. Exemplary application of the system including automotive, photographic and medical endoscopic are also described. The system enables improved image view for and allows customization of views by the end user even after installation of the imaging system.

I claim:

1. An imaging system comprising
a lens, the design of said lens is characterized by a mapping function given by:

$h(\theta)=(f/\beta)*\tan(\beta*\theta)$ for $\beta>0$ $h(\theta)=(f/\beta)*\sin(\beta*\theta)$ for $\beta<0$ where h is the image height formed at the focal plane of the lens, by off-axis rays entering the lens at a field angle θ, f is the effective focal length and β is the rectilinearity of the lens,
an electronic image sensor,
an electronic processor, said electronic processor including a means for accepting a user's input, and,
said processor programmed to acquire, store, display, select images, said images having an overall field of view, accept a user's input, and perform mathematical transformations on said images thereby producing a transformed image,
wherein said mathematical transformations are at least one selected from:
distortion transformation, TV distortion correction, spherical projection, cylindrical projection, and transitional projection.

2. The imaging system of claim 1 wherein the lens is a wide-angle lens comprising 6 elements arranged in three groups, said groups comprising, in order from object to image,
 a. a first group comprising two elements, wherein at least one of the two elements is an aspheric element
 b. a second group comprising a lens element having a positive power, and,
 c. a third group having a positive optical power and comprising a cemented doublet lens and a positive power double convex aspheric lens
and comprising an aperture stop positioned between said second group and said third group.

3. The imaging system of claim 1 wherein the lens is a wide-angle lens comprising 7 elements arranged in three groups, said groups comprising, in order from object to image,
 a. a first group comprising two elements, wherein at least one of the two elements is an aspheric element
 b. a second group comprising a lens element having a positive power, and,
 c. a third group having a positive optical power and comprising: a cemented doublet lens, a positive power double convex lens, and an aspheric element having a varying power, said power positive at the vertex and decreases with increasing radial distance from the vertex,
and comprising an aperture stop positioned between said second group and said third group.

4. The imaging system of claim 1 wherein the mathematical transformation is the distortion transformation and the user's input includes selection of parameters $f_2$ and $\beta_2$, said parameters describing the focal length and rectilinearity of a second lens wherein at least one of the parameters is different from the focal length and rectilinearity of the lens and the transformed image appears as if acquired using a second lens having focal length $f_2$ and rectilinearity $\beta_2$.

5. The imaging system of claim 4 wherein the parameters $f_2$ and $\beta_2$, are constrained to maintain the overall field of view of the original image.

6. The imaging system of claim 1 wherein the imaging systems is used in at least one selected from an endoscope, brachioscope, angioscope and arthroscope.

7. The imaging system of claim 1 used to provide views from the surroundings of an automotive vehicle.

8. The imaging system of claim 1 where the user's inputs are automatically selected by the processor based upon the contents of the digital image data.

9. The imaging system of claim 1 where the means for accepting a user's inputs are at least one selected from: a slider, a rotary knob, and a keyboard.

10. The imaging system of claim 4 wherein the imaging systems is used in at least one selected from an endoscope, brachioscope, angioscopes, colonscopes, laparoscope and arthroscopes.

11. The imaging system of claim 4 used to provide views from the surroundings of an automotive vehicle.

12. The imaging system of claim 4 where the user's inputs are automatically selected by the processor based upon the contents of the digital image data.

13. The imaging system of claim 4 where the means for accepting a user's inputs are at least one selected from: a slider, a rotary knob, and a keyboard.

14. The imaging system of claim 2 wherein the mathematical transformation is the distortion transformation and the user's input includes selection of parameters $f_2$ and $\beta_2$, said parameters describing the focal length and rectilinearity of a second lens wherein at least one of the parameters is different from the focal length and rectilinearity of the lens and the transformed image appears as if acquired using a second lens having focal length $f_2$ and rectilinearity $\beta_2$.

15. The imaging system of claim 14 wherein the parameters $f_2$ and $\beta_2$, are constrained to maintain the overall field of view of the original image.

16. The imaging system of claim 15 where the means for accepting a user's inputs are at least one selected from: a slider, a rotary knob, and a keyboard.

17. The imaging system of claim 15 wherein the imaging systems is used in at least one selected from an endoscope, brachioscope, angioscopes, colonscopes, laparoscope and arthroscopes.

18. The imaging system of claim 15 used to provide views from the surroundings of an automotive vehicle.

19. The imaging system of claim 3 wherein the mathematical transformation is the distortion transformation and the user's input includes selection of parameters $f_2$ and $\beta_2$, said parameters describing the focal length and rectilinearity of a second lens wherein at least one of the parameters is different from the focal length and rectilinearity of the lens and the transformed image appears as if acquired using a second lens having focal length $f_2$ and rectilinearity $\beta_2$.

20. The imaging system of claim 19 wherein the parameters $f_2$ and $\beta_2$, are constrained to maintain the overall field of view of the original image.

21. The imaging system of claim 20 where the means for accepting a user's inputs are at least one selected from: a slider, a rotary knob, and a keyboard.

22. The imaging system of claim 20 wherein the imaging systems is used in at least one selected from an endoscope, brachioscope, angioscopes, colonscopes, laparoscope and arthroscopes.

23. The imaging system of claim 20 used to provide views from the surroundings of an automotive vehicle.

24. A method for transforming a digital image comprising
 acquiring an image from an image sensor using a lens having a focal length, f, and a rectilinearity $\beta$, the design of said lens constrained to follow a mapping function given by:

$$h(\theta)=(f/\beta)*\tan(\beta*\theta) \text{ for } \beta>0$$

$$h(\theta)=(f/\beta)*\sin(\beta*\theta) \text{ for } \beta<0$$

where h is the height from the optical axis of the image of a point formed at the focal plane of the lens, light from said point entering the lens at a field angle $\theta$, said image having an overall field of view
 storing said image in digital memory,
 selecting an image from said digital memory and loading said image into a digital processor,
 acquiring a user's input, said user's input comprising:
  selecting a transformation to apply to the selected image including at least one selected from: distortion transformation, TV distortion correction, spherical projection, cylindrical projection, and transitional projection, and a set of parameters wherein said parameters include a selection of which transformation to be performed and if the selection includes a distortion transformation, said parameters further include parameters $f_2$ and $\beta_2$, said parameters describing the focal length and rectilinearity of a second lens wherein at least one of the parameters $f_2$ and $\beta_2$ is different from the focal length and rectilinearity of the lens, f and $\beta$,
 programming said digital processor to perform the selected transformation on the selected image resulting in a transformed image,
 viewing the transformed image on a display.

25. The imaging system of claim 24 wherein the parameters $f_2$ and $\beta_2$, are constrained to maintain the overall field of view of the original image.

* * * * *